(12) United States Patent
Cunningham et al.

(10) Patent No.: US 9,375,256 B2
(45) Date of Patent: Jun. 28, 2016

(54) ELECTROSURGICAL FORCEPS

(71) Applicant: COVIDIEN LP, Mansfield, MA (US)

(72) Inventors: James S. Cunningham, Boulder, CO (US); Allan J. Evans, Golden, CO (US); Peter M. Mueller, Frederick, CO (US); Nathan White, Longmont, CO (US); David A. Schechter, Boulder, CO (US); Stephen Evans, Westford, MA (US)

(73) Assignee: COVIDIEN LP, Mansfield, MA (US)

( * ) Notice: Subject to any disclaimer, the term of this patent is extended or adjusted under 35 U.S.C. 154(b) by 294 days.

(21) Appl. No.: 14/098,953

(22) Filed: Dec. 6, 2013

(65) Prior Publication Data
US 2014/0221999 A1  Aug. 7, 2014

Related U.S. Application Data

(60) Provisional application No. 61/760,949, filed on Feb. 5, 2013.

(51) Int. Cl.
*A61B 18/14* (2006.01)
*A61B 17/00* (2006.01)

(52) U.S. Cl.
CPC ... *A61B 18/1442* (2013.01); *A61B 2017/00477* (2013.01); *A61B 2018/1455* (2013.01); *A61B 2018/1495* (2013.01)

(58) Field of Classification Search
CPC .......... A61B 18/1445; A61B 18/1442; A61B 18/085; A61B 2018/1455; A61B 2018/00607; A61B 2018/1457; A61B 2018/0063; A61B 2014/1452; A61B 17/29; A61B 17/295; A61B 2017/2939

USPC ..................................................... 606/45–52
See application file for complete search history.

(56) References Cited

U.S. PATENT DOCUMENTS

D249,549 S   9/1978   Pike
D263,020 S   2/1982   Rau, III
(Continued)

FOREIGN PATENT DOCUMENTS

CN   201299462   9/2009
DE   2415263    10/1975
(Continued)

OTHER PUBLICATIONS

U.S. Appl. No. 08/926,869, filed Sep. 10, 1997, James G. Chandler.
(Continued)

*Primary Examiner* — Michael Peffley

(57) ABSTRACT

An electrosurgical forceps is provided. The electrosurgical forceps includes a housing having a shaft extending distally therefrom. The shaft defines a longitudinal axis therethrough and a knife blade shaft is operably disposed within the shaft. An end effector is operably disposed at a distal end of the shaft. The end effector includes a pair of spaced-apart first and second jaw members that are movable from an open configuration to a clamping configuration. An electrode assembly includes first and second electrode housings and a knife blade. The first and second electrode housings are operably coupled to one another and are configured to selectively couple to respective first and second jaw members to electrosurgically treat tissue clamped between the first and second jaw members. The knife blade is configured to selectively couple to the knife blade shaft.

15 Claims, 16 Drawing Sheets

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | Decarolis |
| D343,453 S | 1/1994 | Noda |
| 5,308,358 A * | 5/1994 | Bond ............... A61B 17/29 606/170 |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,445,638 A | 8/1995 | Rydell et al. |
| 5,456,684 A | 10/1995 | Schmidt et al. |
| 5,458,598 A | 10/1995 | Feinberg et al. |
| 5,599,351 A | 2/1997 | Haber et al. |
| D384,413 S | 9/1997 | Zlock et al. |
| H1745 H | 8/1998 | Paraschac |
| 5,800,449 A | 9/1998 | Wales |
| 5,826,776 A | 10/1998 | Schulze et al. |
| 5,827,279 A | 10/1998 | Hughett et al. |
| D402,028 S | 12/1998 | Grimm et al. |
| D408,018 S | 4/1999 | McNaughton |
| 5,938,027 A | 8/1999 | Soroff et al. |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| 6,216,868 B1 | 4/2001 | Rastegar et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| 6,443,970 B1 | 9/2002 | Schulze et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| 6,916,314 B2 * | 7/2005 | Schneider ........ A61B 17/00234 606/1 |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,679,140 B2 | 3/2014 | Butcher |
| RE44,834 E | 4/2014 | Dumbauld |
| 2007/0213708 A1 | 9/2007 | Dumbauld et al. |
| 2008/0058802 A1 | 3/2008 | Couture et al. |
| 2008/0319442 A1 * | 12/2008 | Unger ............. A61B 18/1445 606/48 |
| 2011/0251606 A1 | 10/2011 | Kerr |
| 2011/0319888 A1 * | 12/2011 | Mueller ........... A61B 18/1445 606/41 |
| 2013/0018411 A1 | 1/2013 | Collings et al. |
| 2013/0030432 A1 | 1/2013 | Garrison et al. |
| 2013/0085516 A1 | 4/2013 | Kerr et al. |
| 2014/0025070 A1 * | 1/2014 | Kerr ................ A61B 18/1445 606/45 |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0052128 A1 | 2/2014 | Townsend et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 3627221 | 2/1988 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 1281878 | 10/2005 |
| EP | 2272454 A1 | 1/2011 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47149 | 2/1999 |
| JP | 11-47150 | 2/1999 |
| JP | 11-169381 | 6/1999 |
| JP | 11-192238 | 7/1999 |
| JP | 11-244298 | 9/1999 |
| JP | 2000-135222 | 5/2000 |

(56) References Cited

FOREIGN PATENT DOCUMENTS

| | | |
|---|---|---|
| JP | 2000-342599 | 12/2000 |
| JP | 2000-350732 | 12/2000 |
| JP | 2001-8944 | 1/2001 |
| JP | 2001-29355 | 2/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2005-312807 | 10/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 2005/110264 | 11/2005 |
| WO | WO 2006/021269 | 3/2006 |
| WO | WO 2008/040483 | 4/2008 |
| WO | WO 2011/018154 | 2/2011 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 13/731,674, filed Dec. 31, 2012, Siebrecht.
U.S. Appl. No. 14/019,031, filed Sep. 5, 2013, Garrison.
U.S. Appl. No. 14/019,094, filed Sep. 5, 2013, Garrison.
U.S. Appl. No. 14/032,486, filed Sep. 20, 2013, Kendrick.
U.S. Appl. No. 14/035,423, filed Sep. 24, 2013, Garrison.
U.S. Appl. No. 14/037,772, filed Sep. 26, 2013, Frushour.
U.S. Appl. No. 14/041,995, filed Sep. 30, 2013, Kendrick.
U.S. Appl. No. 14/042,947, filed Oct. 1, 2013, Craig.
U.S. Appl. No. 14/043,039, filed Oct. 1, 2013, Rusin.
U.S. Appl. No. 14/043,322, filed Oct. 1, 2013, O'Neil.
U.S. Appl. No. 14/047,474, filed Oct. 7, 2013, Mueller.
U.S. Appl. No. 14/050,593, filed Oct. 10, 2013, Plaven.
U.S. Appl. No. 14/052,827, filed Oct. 14, 2013, Nau.
U.S. Appl. No. 14/052,856, filed Oct. 14, 2013, Latimer.
U.S. Appl. No. 14/052,871, filed Oct. 14, 2013, Kappus.
U.S. Appl. No. 14/054,173, filed Oct. 15, 2013, Payne.
U.S. Appl. No. 14/054,573, filed Oct. 15, 2013, Harper.
U.S. Appl. No. 14/064,310, filed Oct. 28, 2013, Reschke.
U.S. Appl. No. 14/065,644, filed Oct. 29, 2013, Reschke.
U.S. Appl. No. 14/080,564, filed Nov. 14, 2013, Lawes.
U.S. Appl. No. 14/080,581, filed Nov. 14, 2013, Kerr.
U.S. Appl. No. 14/083,696, filed Nov. 19, 2013, Horner.
U.S. Appl. No. 14/086,399, filed Nov. 21, 2013, Allen.
U.S. Appl. No. 14/091,505, filed Nov. 27, 2013, Garrison.
U.S. Appl. No. 14/091,521, filed Nov. 27, 2013, Garrison.
U.S. Appl. No. 14/091,532, filed Nov. 27, 2013, Garrison.
U.S. Appl. No. 14/098,953, filed Dec. 6, 2013, Cunningham.
U.S. Appl. No. 14/100,237, filed Dec. 9, 2013, Reschke.
U.S. Appl. No. 14/103,971, filed Dec. 12, 2013, Roy.
U.S. Appl. No. 14/105,374, filed Dec. 13, 2013, Moua.
U.S. Appl. No. 14/109,459, filed Dec. 17, 2013, Hoarau.
U.S. Appl. No. 14/149,343, filed Jan. 7, 2014, Schmaltz.
U.S. Appl. No. 14/152,618, filed Jan. 10, 2014, Artale.
U.S. Appl. No. 14/152,690, filed Jan. 10, 2014, Hart.
U.S. Appl. No. 14/153,346, filed Jan. 13, 2014, Collings.
U.S. Appl. No. 14/162,192, filed Jan. 23, 2014, Garrison.
U.S. Appl. No. 14/164,569, filed Jan. 27, 2014, Heard.
U.S. Appl. No. 14/169,358, filed Jan. 31, 2014, Reschke.
U.S. Appl. No. 14/172,050, filed Feb. 4, 2014, Johnson.
U.S. Appl. No. 14/173,391, filed Feb. 5, 2014, Kharin.
U.S. Appl. No. 14/176,341, filed Feb. 10, 2014, Hart.
U.S. Appl. No. 14/176,684, filed Feb. 10, 2014, Chojin.
U.S. Appl. No. 14/177,812, filed Feb. 11, 2014, Dycus.
U.S. Appl. No. 14/178,540, filed Feb. 12, 2014, Anderson.
U.S. Appl. No. 14/182,894, filed Feb. 18, 2014, Hart.
U.S. Appl. No. 14/182,967, filed Feb. 18, 2014, Latimer.
U.S. Appl. No. 14/183,090, filed Feb. 18, 2014, Arts.
U.S. Appl. No. 14/188,935, filed Feb. 25, 2014, Reschke.
U.S. Appl. No. 14/196,066, filed Mar. 4, 2014, McCullough.
U.S. Appl. No. 14/204,770, filed Mar. 11, 2014, Dumbauld.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales-Product Literature; Dec. 31, 2000.
Johnson et al. "Evaluation of a Bipolar Electrothermal Vessel Sealing Device in Hemorrhoidectomy" Sales-Product Literature; Jan. 2004.
E. David Crawford "Evaluation of a New Vessel Sealing Device in Urologic Cancer Surgery" Sales-Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales-Product Literature 1999.
LigaSure Vessel Sealing System, the Seal of Confidence in General, Gynecologic, Urologic, and Laparaoscopic Surgery; Sales-Product Literature; Apr. 2002.
Joseph Ortenberg "LigaSure System Used in Laparoscopic 1st and 2nd Stage Orchiopexy" Innovations That Work, Nov. 2002.

(56) References Cited

OTHER PUBLICATIONS

Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales-Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales-Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul.-Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales-Product Literature 2000.
Jarrett et al., "Use of the LigaSure Vessel Sealing System for Peri-Hilar Vessels in Laparoscopic Nephrectomy" Sales-Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales-Product Literature 1999.
International Search Report and Written Opinion of the International Searching Authority, corresponding to International Application No. PCT/US2013/074136, dated Mar. 31, 2014; 13 Pages.

\* cited by examiner

ELECTROSURGICAL FORCEPS

CROSS REFERENCE TO RELATED APPLICATION

The present application claims the benefit of and priority to U.S. Provisional Application Ser. No. 61/760,949, filed on Feb. 5, 2013, the entire contents of which are incorporated herein by reference.

BACKGROUND

1. Technical Field

The present disclosure relates to an electrosurgical forceps. More particularly, the present disclosure relates to an electrosurgical forceps including a selectively removable electrode assembly with a knife blade operably coupled thereto.

2. Description of Related Art

Electrosurgical forceps that are configured to electrosurgically treat and, subsequently, sever tissue are well known in the art. Electrosurgical forceps of this type typically include a housing, a shaft, a handle assembly, an end effector including a pair of opposing jaw members and a knife blade assembly.

In use of the aforementioned electrosurgical forceps, tissue may be positioned and clamped between the jaw members. Subsequently, electrosurgical energy may be applied to one or more electrodes of the jaw members to electrosurgically treat, e.g., seal, coagulate, etc., the tissue. Thereafter, a knife blade of the knife blade assembly may be advanced through the jaw members to sever the electrosurgically treated tissue.

The aforementioned electrosurgical forceps may only be reliable to sever tissue for a limited amount of applications as a result of the knife blade dulling over time. Traditionally, this was solved by using electrosurgical forceps that were entirely disposable; this can be costly to an end user and/or a supplier, e.g., a surgeon and/or hospital.

SUMMARY

As can be appreciated, an electrosurgical forceps including a selectively removable electrode assembly including a knife blade operably coupled thereto may prove useful in the surgical arena.

Embodiments of the present disclosure are described in detail with reference to the drawing figures wherein like reference numerals identify similar or identical elements. As used herein, the term "distal" refers to the portion of a surgical instrument that is being described which is further from a user, while the term "proximal" refers to the portion of the surgical instrument that is being described which is closer to a user.

An aspect of the present disclosure provides an electrosurgical forceps. The electrosurgical forceps includes a housing that has a shaft extending distally therefrom. The shaft defines a longitudinal axis therethrough and a knife blade shaft is operably positioned within the shaft. An end effector is operably disposed at a distal end of the shaft. The end effector includes a pair of spaced-apart first and second jaw members that are movable from an open configuration to a clamping configuration. An electrode assembly includes first and second electrode housings and a knife blade. The first and second electrode housings are operably coupled to one another and configured to selectively couple to respective first and second jaw members to electrosurgically treat tissue clamped between the first and second jaw members. The knife blade is configured to selectively couple to the knife blade shaft.

The electrosurgical forceps may include a trigger assembly that operably couples to the knife blade shaft for moving the knife blade shaft and knife blade along the longitudinal axis. Moreover, a distal end of the knife blade shaft may include one or more mechanical interfaces that are configured to releasably couple to one or more corresponding mechanical interfaces disposed at a proximal end of the knife blade. The mechanical interface(s) on the knife blade may be in the form of a notch and the corresponding mechanical interface(s) on the knife blade shaft may be in the form of a boss having a shape that complements the notch. The knife blade shaft including the boss may be rotatable about the longitudinal axis to allow the boss to engage the notch of the knife blade.

The electrosurgical forceps may include a selector switch that is configured to rotate the knife blade shaft including the boss. The selector switch may include a plurality of teeth that are configured to mesh with a blade shaft spur gear disposed at a proximal end of the knife blade shaft.

One or both of the first and second electrode housings may include a lock tab that is configured to selectively engage a corresponding notch on one or both of the first and second jaw members to facilitate coupling the first and second electrodes to the first and second jaw members. The lock tab may be resilient and in the form of a t-clip. The lock tab may be positioned on an insulative substrate of one of the first and second jaw members.

An aspect of the present disclosure provides an electrosurgical forceps. The electrosurgical system includes an electrosurgical generator. The electrosurgical forceps includes a housing having a shaft extending distally therefrom. The shaft defines a longitudinal axis therethrough. A knife blade shaft is operably positioned within the shaft and is rotatable about the longitudinal axis. An end effector includes a pair of spaced-apart first and second jaw members and is movable from an open configuration to a clamping configuration. An electrode assembly includes first and second electrode housings and a knife blade. The first and second electrode housings configured to selectively couple to respective first and second jaw members of the electrosurgical forceps for electrosurgically treating tissue clamped between the first and second jaw members. The knife blade includes a proximal end configured to selectively couple to a distal end of the knife blade shaft when the knife blade shaft is rotated about the longitudinal axis.

The electrosurgical forceps may include a trigger assembly that operably couples to the knife blade shaft for moving the knife blade shaft and knife blade along the longitudinal axis. Moreover, a distal end of the knife blade shaft may include one or more mechanical interfaces that are configured to releasably couple to one or more corresponding mechanical interfaces disposed at a proximal end of the knife blade. The mechanical interface(s) on the knife blade may be in the form of a notch and the corresponding mechanical interface(s) on the knife blade shaft may be in the form of a boss having a shape that complements the notch. The knife blade shaft including the boss may be rotatable about the longitudinal axis to engage the notch of the knife blade.

The electrosurgical forceps may include a selector switch that is configured to rotate the knife blade shaft including the boss. The selector switch may include a plurality of teeth that are configured to mesh with a blade shaft spur gear disposed at a proximal end of the knife blade shaft.

One or both of the first and second electrode housings may include a lock tab that is configured to selectively engage a corresponding notch on one or both of the first and second jaw members to facilitate coupling the first and second electrodes to the first and second jaw members. The lock tab may be resilient and in the form of a t-clip. The lock tab may be positioned on an insulative substrate of one of the first and second jaw members.

As aspect of the present disclosure provides a method for electrosurgically treating tissue. An electrosurgical forceps is provided. The electrosurgical forceps includes a housing having a shaft defining a longitudinal axis therethrough, a knife blade shaft operably positioned within the shaft and rotatable about the longitudinal axis, and an end effector including a pair of spaced-apart first and second jaw members that are movable from an open configuration to a clamping configuration. Thereafter, an electrode assembly is provided. The electrode assembly includes first and second electrode housings and a knife blade to the first and second jaw members, respectively. Subsequently, the knife blade is coupled to the knife blade shaft. And, electrodes of the electrode assembly are energized to electrosurgically treat tissue.

The electrosurgically treated tissue may be severed with the knife blade. Moreover, the knife blade shaft may be provided with one or more mechanical interfaces that may be configured to releasably couple to one or more corresponding mechanical interfaces disposed at a proximal end of the knife blade. Further, one (or both) of the first and second electrode housings may be provided with a lock tab that is configured to selectively engage a corresponding notch on one (or both) of the first and second jaw members to facilitate coupling the first and second electrode housings to the first and second jaw members.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In accordance with the instant disclosure, a reusable electrosurgical device that utilizes a disposable electrode assembly is provided. The electrode assembly is configured to releasably couple to jaw members of the electrosurgical device and utilizes a knife blade that is configured to releasably couple to a blade shaft of the electrosurgical device. After a surgical procedure, the disposable electrode assembly including the knife blade may be uncoupled from the electrosurgical device and a new or re-sterilized disposable electrode assembly and/or knife blade may be coupled to the electrosurgical device and utilized to treat tissue.

Figure 1:
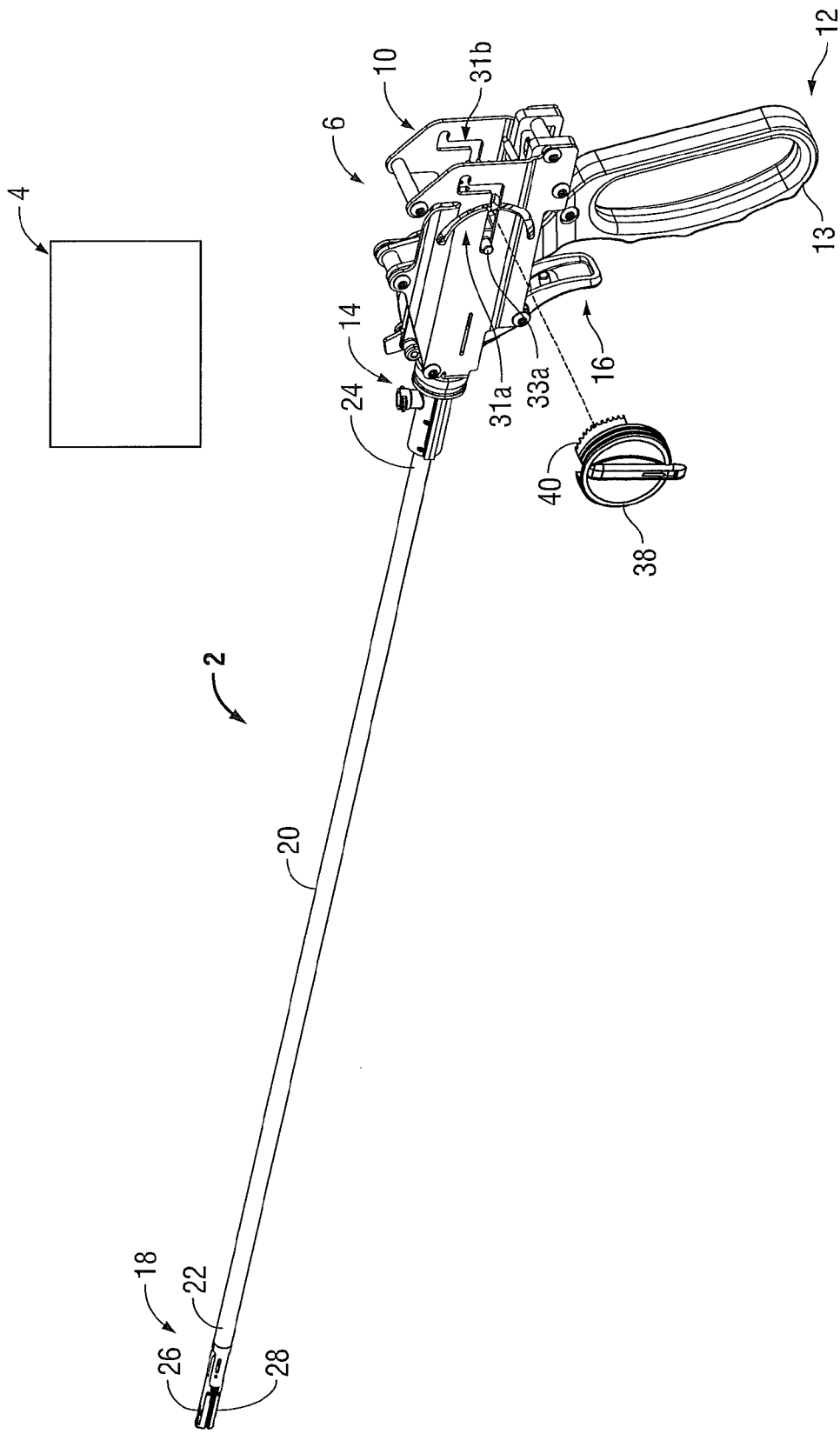
FIG. 1 is a left, perspective view of an endoscopic bipolar forceps having a selectively removable electrode assembly with a knife blade according to an embodiment of the present disclosure.

Turning now to FIG. 1, an electrosurgical system 2 is illustrated including a generator 4, an electrosurgical device (e.g., an electrosurgical endoscopic forceps 6 (forceps 6) configured for use in closed laparoscopic procedures) and an electrode assembly 8 (see FIGS. 2-5).

Continuing with reference to FIG. 1, forceps 6 includes a housing 10, a handle assembly 12, a rotating assembly 14, a trigger assembly 16 and an end effector assembly 18. Forceps 6 further includes a shaft 20 having a distal end 22 configured to mechanically engage end effector assembly 18 and a proximal end 24 that mechanically engages housing 10. Forceps 6 also includes electrosurgical cable (not explicitly shown) that connects forceps 6 to generator 4 or other suitable power source. One or more wires (not explicitly shown) of suitable configuration may extend through the cable and through shaft 20 for positioning adjacent jaw members 26, 28 in order to provide electrical energy to at least one of jaw members 26, 28 of end effector assembly 18.

Figure 2:
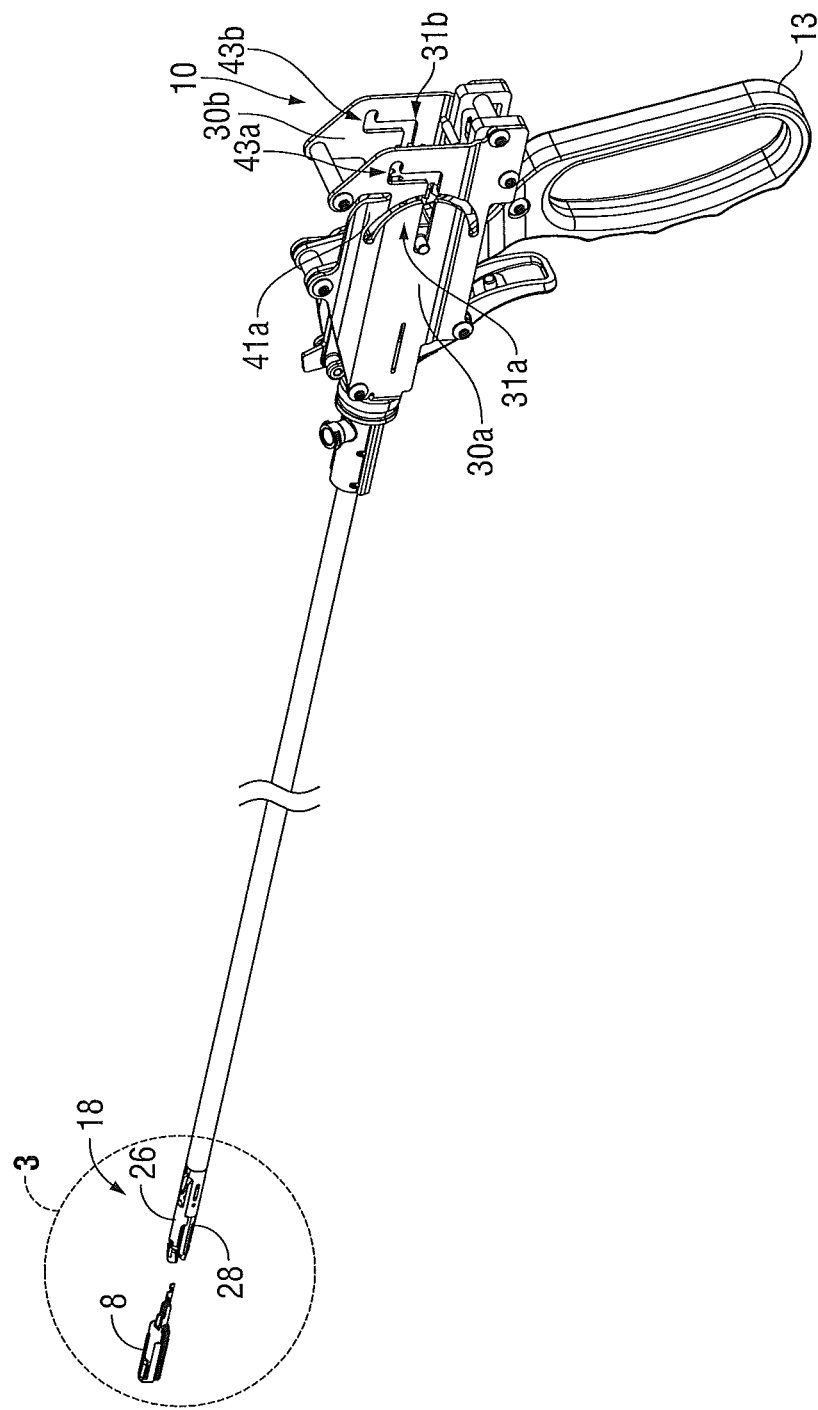
FIG. 2 is a left, perspective view of the endoscopic bipolar forceps depicted in FIG. 1 with the electrode assembly unattached to the endoscopic bipolar forceps.
Figure 3:
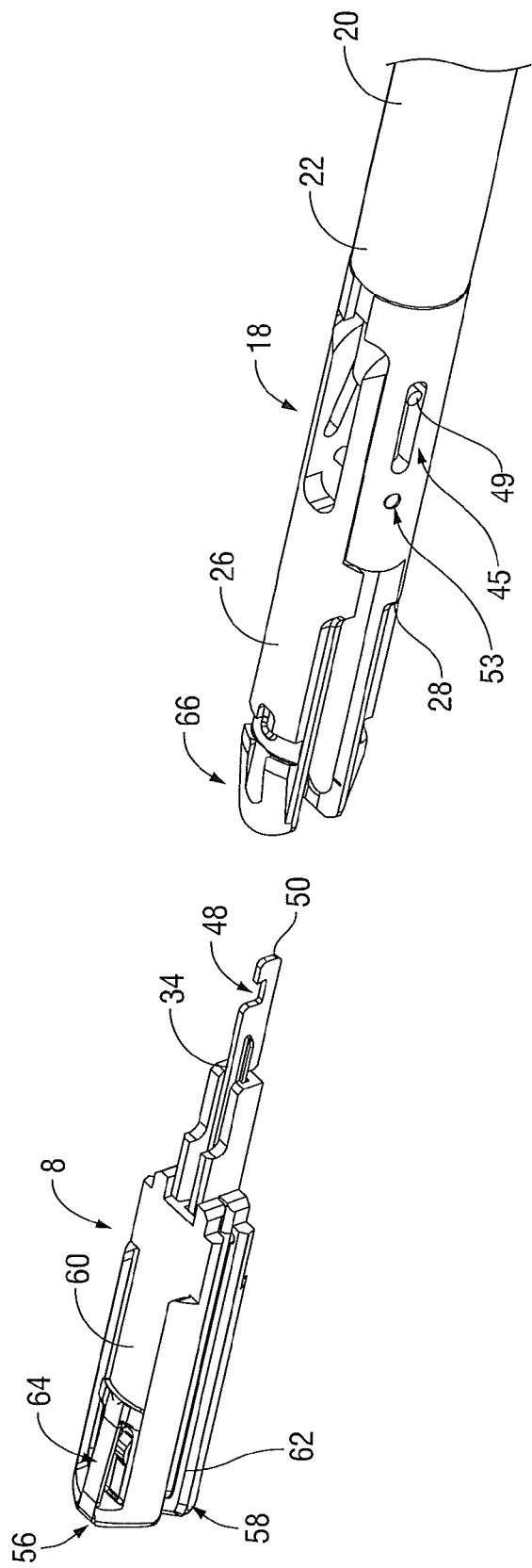
FIG. 3 is an enlarged, perspective view of the area of detail of FIG. 2.
Figure 6:
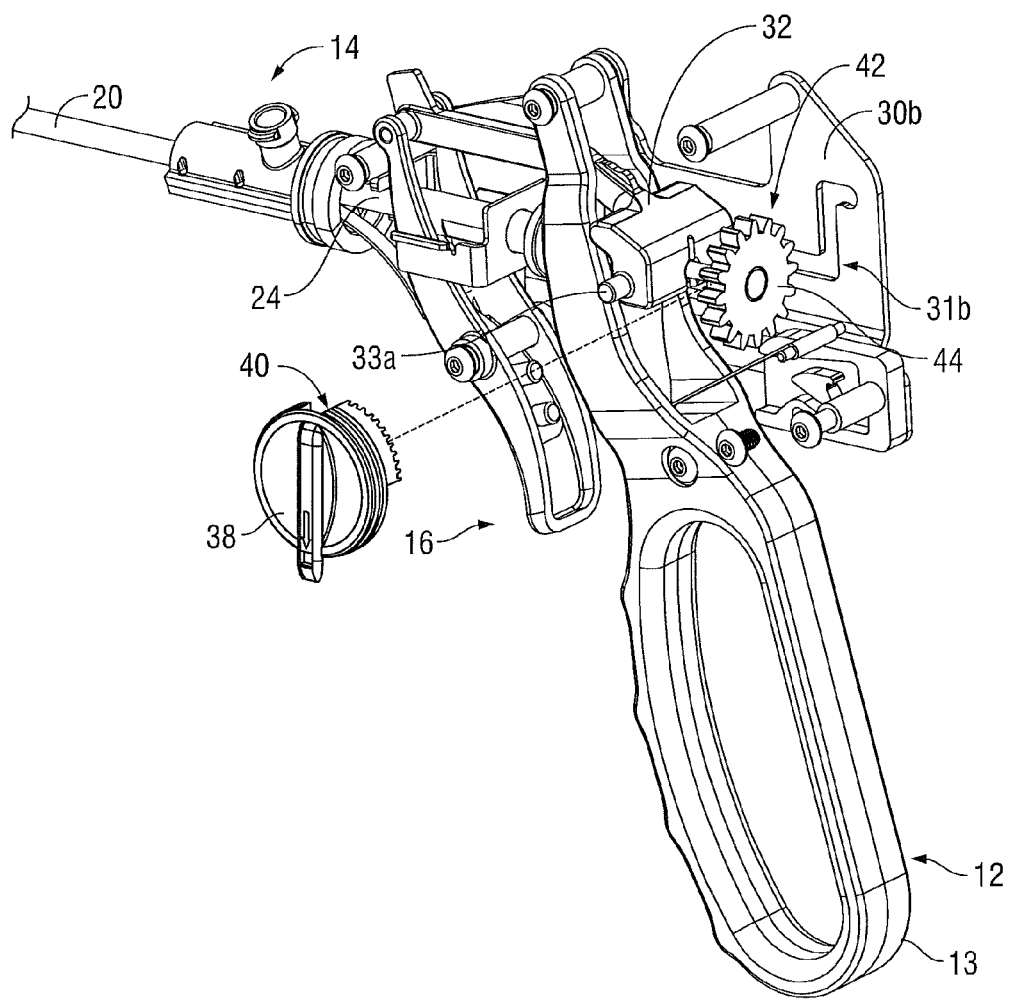
FIG. 6 is a left, perspective view of a proximal end of the endoscopic bipolar forceps with a left internal frame removed to illustrate the operative components contained within a housing of the endoscopic bipolar forceps.
Figure 16:
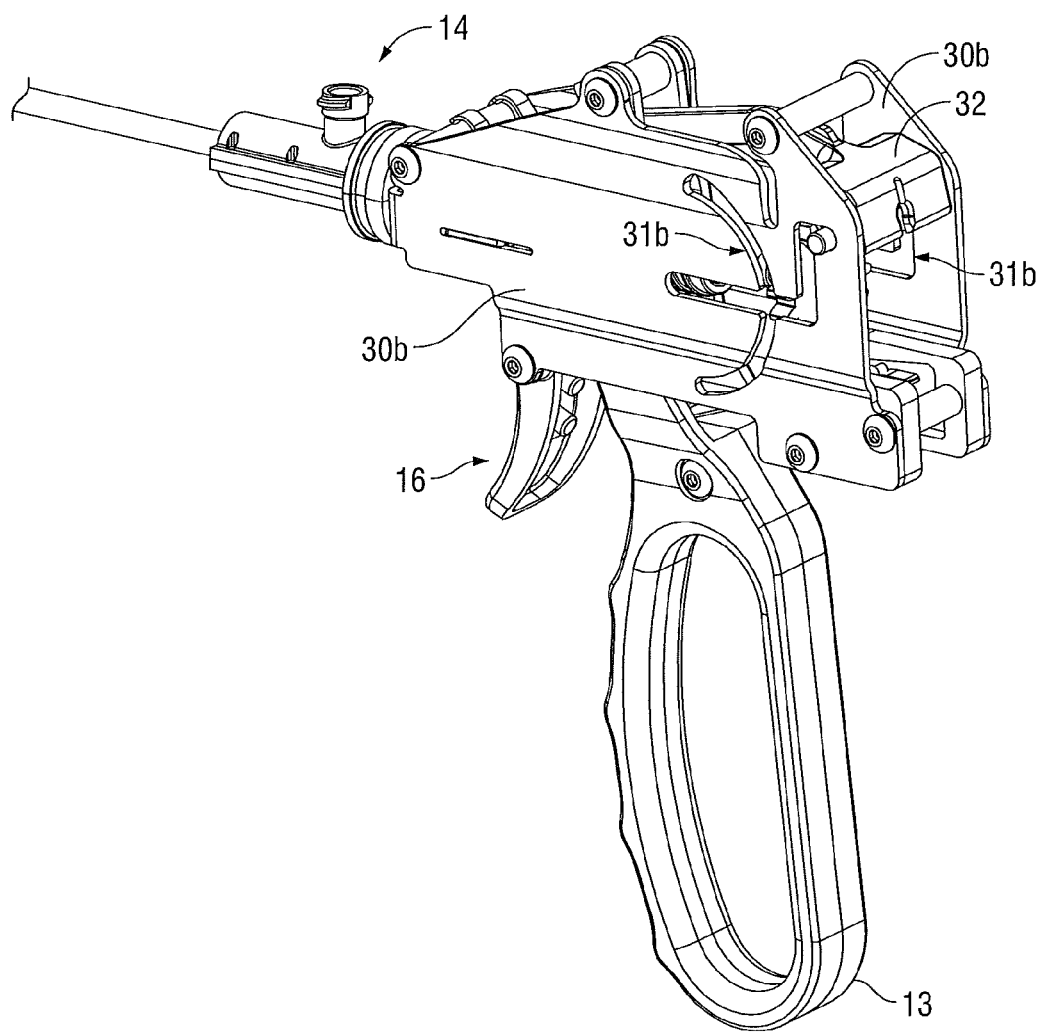
FIG. 16 is a partial, left perspective view of the proximal end of the endoscopic bipolar forceps illustrating a position of the trigger link prior to sterilizing the endoscopic bipolar forceps.

With continued reference to FIG. 1, and with reference to FIGS. 1-2, 6, 9-10 and 16, housing 10 includes left and right exterior half portions (not explicitly shown) that are supported by corresponding internal left and right frame portions 30*a*, 30*b* (see FIG. 2 for example). The left and right exterior half portions are not shown to illustrate one or more components contained within housing 10. Left and right frame portions 30*a*, 30*b* are coupled to one another via one or more spacer and dowel pins configurations or other suitable configurations (e.g., rivets, pins or the like). Each of left and right frame portions 30*a*, 30*b* includes a grooved area 31*a*, 31*b* of suitable configuration that is configured to receive a corresponding left nub 33*a* (see FIGS. 1 and 6 for example), and right nub (not explicitly shown) of a blade link 32 (FIGS. 6 and 16).

Figure 5:
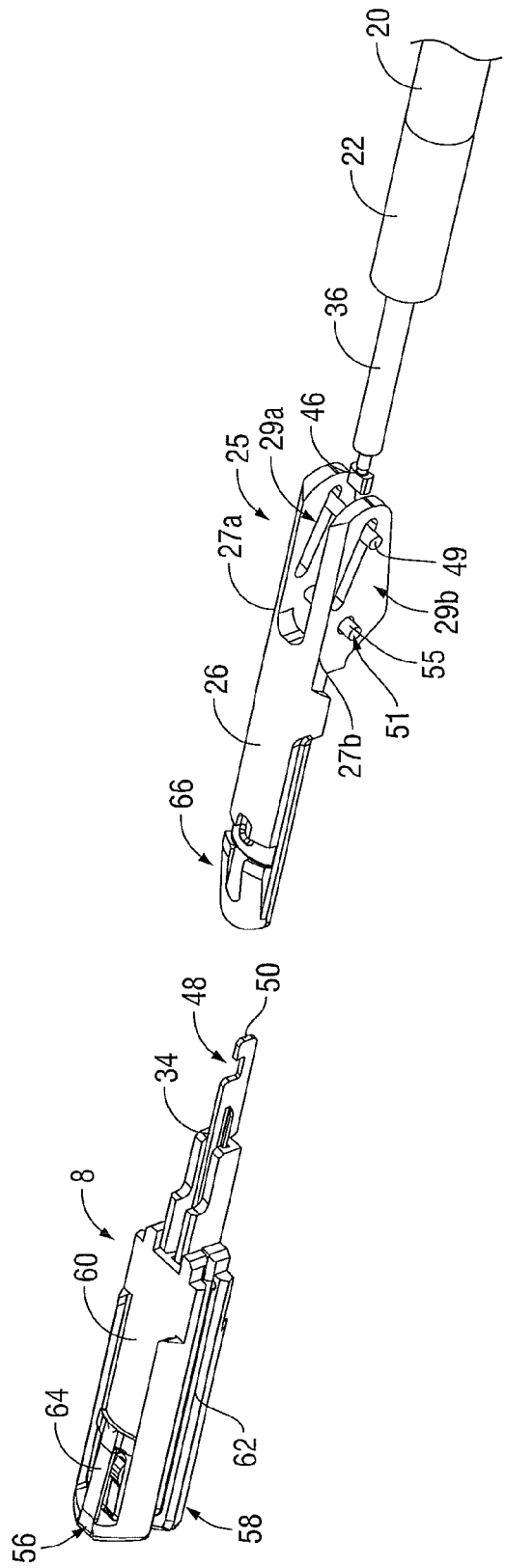
FIG. 5 is an enlarged perspective view of the distal end of the endoscopic bipolar forceps with a lower jaw housing and jaw shaft tip removed to illustrate a knife blade shaft.

Blade link 32 operably couples to trigger assembly 16 via one or more suitable coupling methods, e.g., rivet, pin, levers or the like, and is configured to facilitate sterilization of forceps 6. Specifically, blade link 32 couples trigger assembly 16 to a knife blade shaft 36 (knife blade shaft 36 is illustrated in FIG. 5 for example). When blade link 32 is lifted, knife blade shaft 36 may be removed for sterilization. Blade link 32 is accessible by removing the left and right exterior half portions so that an end user may position left nub 33*a* and the right nub in corresponding left and right upper portions 43*a* and 43*b* of grooved areas 31*a*, 31*b* (see FIG. 2 for example). With left nub 33*a* and the right nub of blade link 32 in this configuration, forceps 6 may be sterilized.

Referring to FIGS. 1 and 6, selector switch 38 includes a generally circumferential shape and is positioned on one of the exterior left and right exterior half portions of housing 10 for manual manipulation thereof. For illustrative purposes, selector switch 38 is shown operable from the left exterior half portion. Selector switch 38 includes a plurality of teeth 40 that extend through an arcuate portion 41*a* (see FIGS. 2 and 10 for example) of grooved area 31*a*. Selector switch 38 is positioned on the left exterior half portion so that left nub 33*a* and the right nub of blade link 32 may be moved through respective grooved areas 31*a*, 31*b*. Plurality of teeth 40 are configured to mesh with a corresponding plurality of teeth 42 that are disposed on a blade shaft spur gear 44 (see FIGS. 6 and 10) when selector switch 38 is rotated, e.g., in either a clockwise or counter-clockwise direction.

Blade shaft spur gear 44 operably couples to knife blade shaft 36 (FIGS. 5, 7-8 and 11-15) via one or more suitable coupling methods, e.g., press-fit, soldering, or other suitable coupling methods, and is configured to rotate knife blade shaft 36 and a knife blade boss 46 (FIGS. 5, 7-8 and 11-15) disposed thereon for coupling and uncoupling electrode assembly 8 including knife blade 34 to and from jaws 26, 28. Specifically, rotation of selector switch 38 causes the plurality of teeth 40 to mesh with plurality of teeth 42 which, in turn, causes knife blade shaft 36 to rotate which, in turn, causes knife blade boss 46 to also rotate and engage or disengage a corresponding notch 48 disposed at a proximal end 50 of knife blade 34 (see FIGS. 2-5, 7-8 and 11-15).

When selector switch 38 is rotated to a load/unload configuration (e.g., to couple/uncouple knife blade 34 to and from knife blade shaft 36), the blade shaft spur gear 44, knife blade shaft 36 and knife blade boss 46 are disengaged from notch 48, and these components may be removed/inserted from the proximal end of housing 10. In embodiments, this may be accomplished by first disengaging blade link 32 from a shoulder drive feature (not explicitly shown) on blade shaft 36. In accordance with the instant disclosure, blade link 36 may be moved proximally in grooved area 31*a*, 31*b* such that left nub 33*a* (and the right nub) may be moved into a "parked" configuration. Accordingly, this disengages a pocket (not explicitly shown) of blade link 32 that captures the shoulder drive feature in knife blade shaft 36; this pocket serves as a "yoke" on knife blade shaft 36. The "yoke" feature allows rotation and axial motion of knife blade shaft 36 as a result of the "yoke" feature translating knife blade shaft 36 through movement of the associated knife trigger links. After reinstallation of knife blade shaft 36, blade link 32 may be repositioned and the pocket may be engaged with the shoulder drive feature of the knife blade shaft 36.

While knife blade boss 46 and notch 48 have been described herein as being utilized as a mechanical interface configuration to couple and uncouple knife blade 34 from knife blade shaft 36, other mechanical interfaces are contemplated. For example, a "hook and eye" mechanical interface configuration or an "indent/detent" mechanical interface configuration, or other suitable mechanical interface configurations may be utilized to couple and uncouple knife blade 34 from knife blade shaft 36.

Knife blade shaft 36 is positioned and extends within shaft 20 and operably couples to trigger assembly 14 to effectuate translation of knife blade shaft 36 for translating knife blade 34 through the jaws 26, 28 to sever tissue that has been electrosurgically treated. Moreover, knife blade shaft 36 extends within housing 10 and operably couples to selector switch 38 via blade shaft spur gear 44 to effectuate rotation of knife blade shaft 36 for coupling and uncoupling knife blade 34 from knife blade shaft 36.

Figure 11:
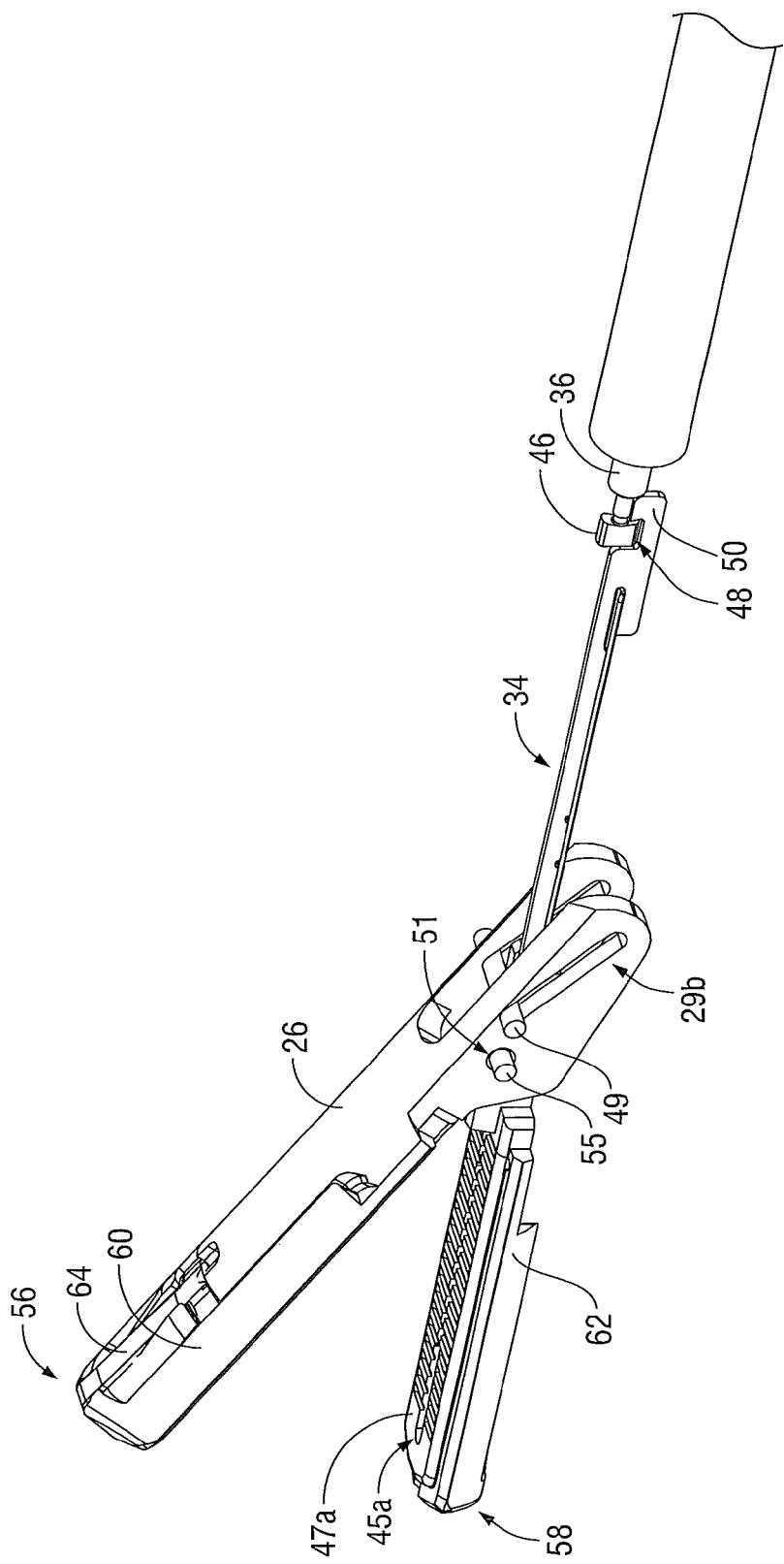
FIG. 11 is a partial, left perspective view of the distal end of the endoscopic bipolar forceps with the jaw shaft tip removed to illustrate the knife blade shaft and knife blade engaged with one another when the jaw members are in an open configuration.
Figure 12:
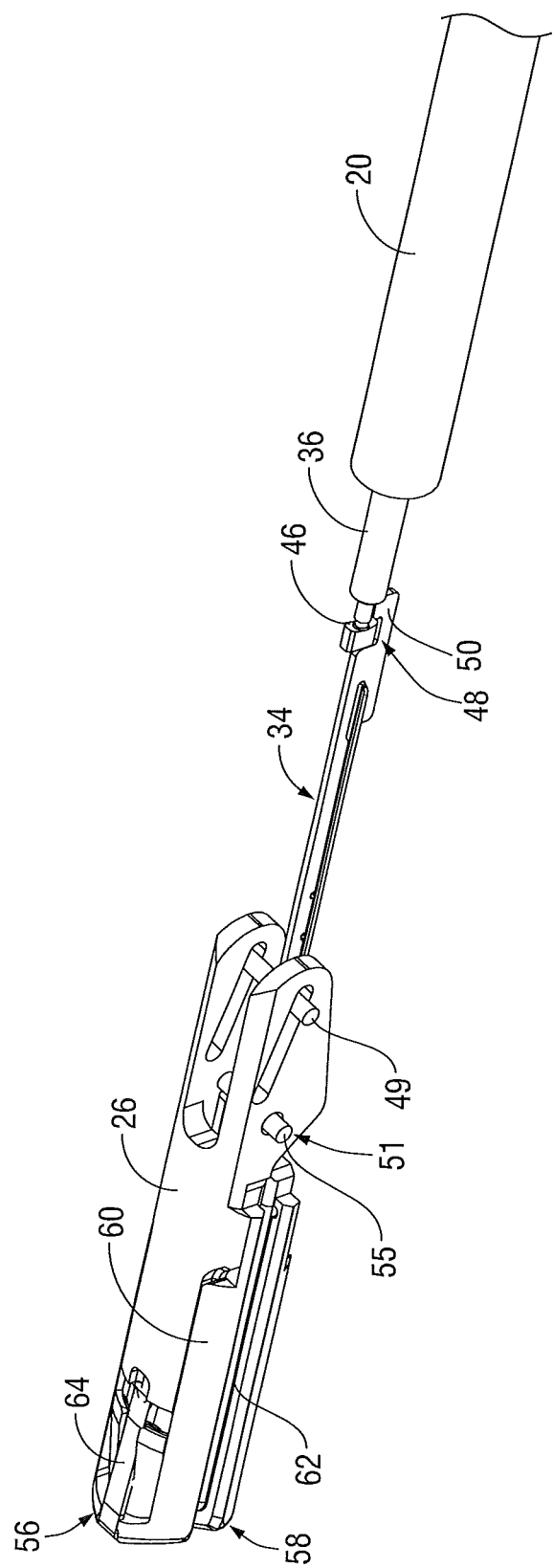
FIG. 12 is a partial, left perspective view of the distal end of the endoscopic bipolar forceps with the jaw shaft tip removed to illustrate the knife blade shaft and knife blade engaged with one another when the jaw members are in a closed configuration.
Figure 13:
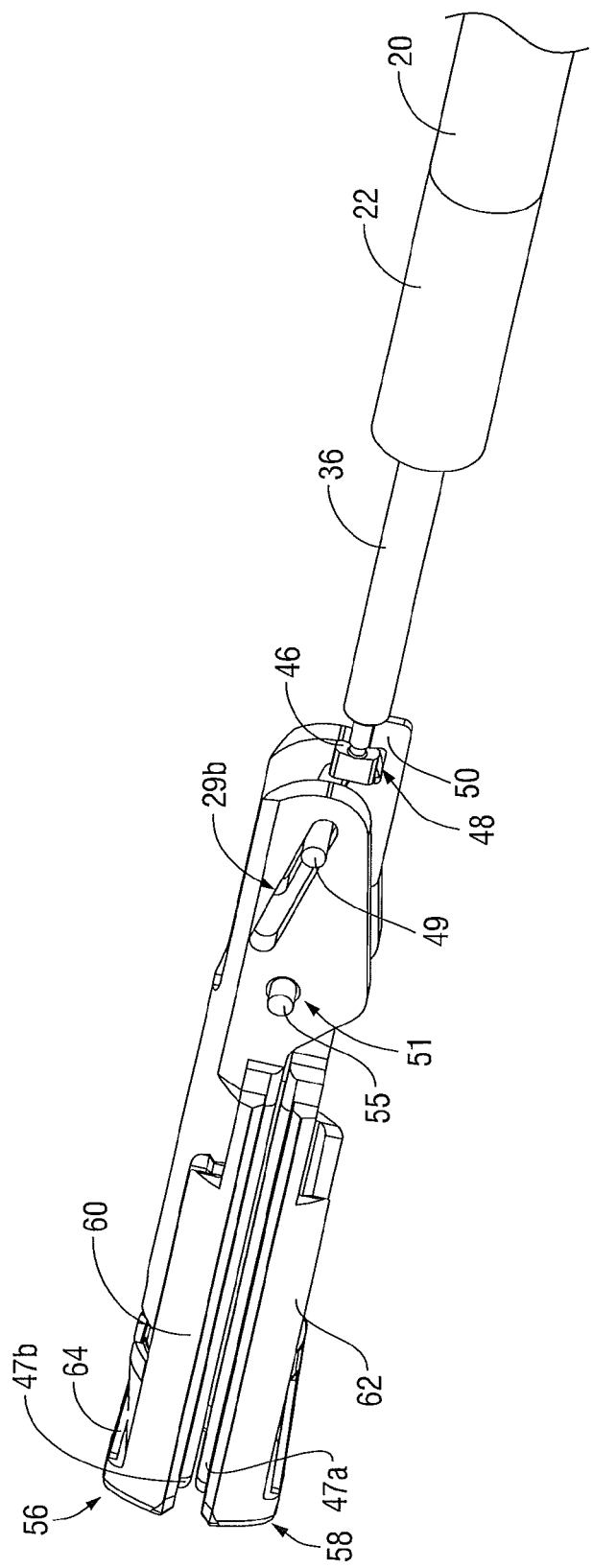
FIG. 13 is a partial, left perspective view of the distal end of the endoscopic bipolar forceps with the jaw shaft tip removed to illustrate the knife blade shaft and knife blade engaged with one another when the jaw members are in a closed configuration and the cutting shaft and cutting blade are in an extended configuration.

Knife blade 34 operably couples to electrode assembly 8 and is configured to translate through a corresponding knife channel 45*a* defined through a second electrode 47*a* (as best seen in FIG. 11) and a corresponding knife channel (not explicitly shown) defined through a first electrode 47*b* (FIG. 13). In the illustrated embodiment, knife blade 34 securely couples to electrode assembly 8 such that knife blade 34 is prevented from becoming separated therefrom. Alternatively, knife blade 34 may be configured for removal from electrode assembly 34. This particular embodiment is useful when knife blade 34 is disposable and electrode assembly 8 is configured for sterilization and reuse. In this particular embodiment, a new or sterile knife blade 34 (that has been previously sterilized via one more sterilization processes, e.g., autoclave) may be coupled to electrode assembly 8 and electrode assembly 8 including new knife blade 34 may be coupled to jaws 26, 28.

Figure 14:
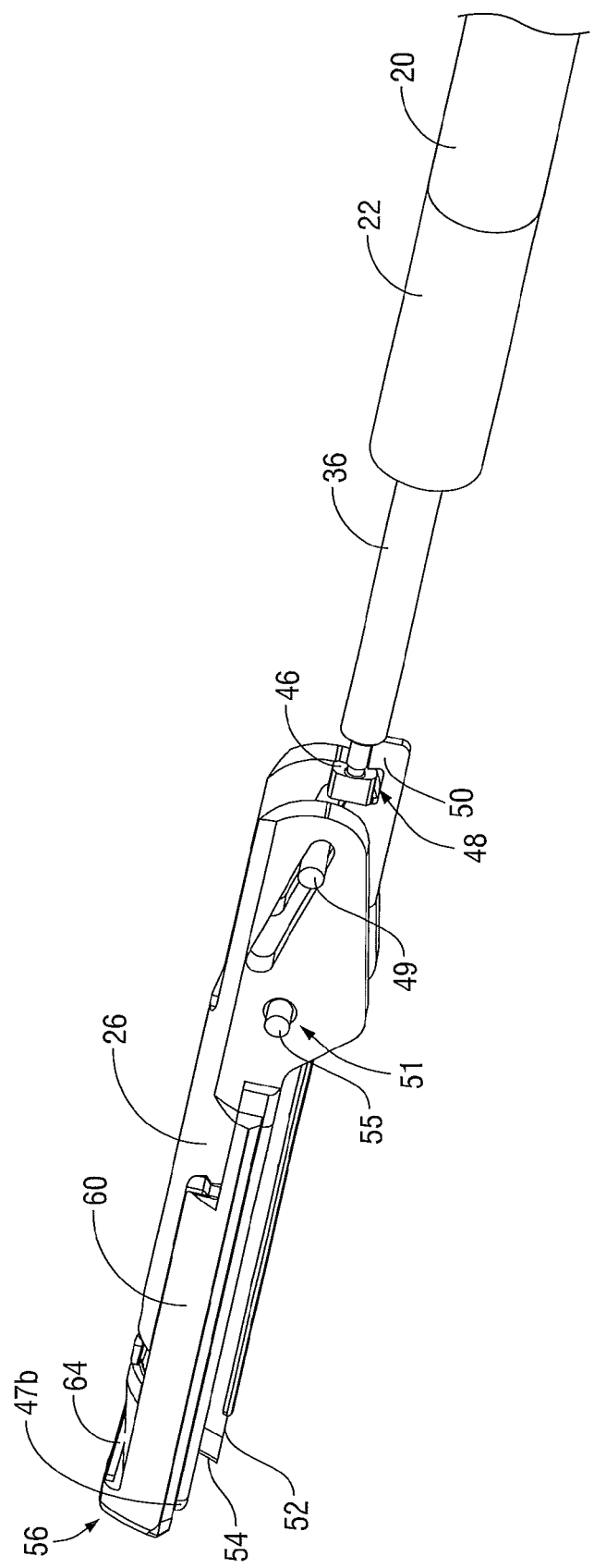
FIG. 14 is a partial, left perspective view of the distal end of the endoscopic bipolar forceps with the jaw shaft tip, lower electrode assembly and jaw member removed to illustrate the knife blade shaft and knife blade engaged with one another when the jaw members are in a closed configuration and the cutting shaft and cutting blade are in an extended configuration.
Figure 15:
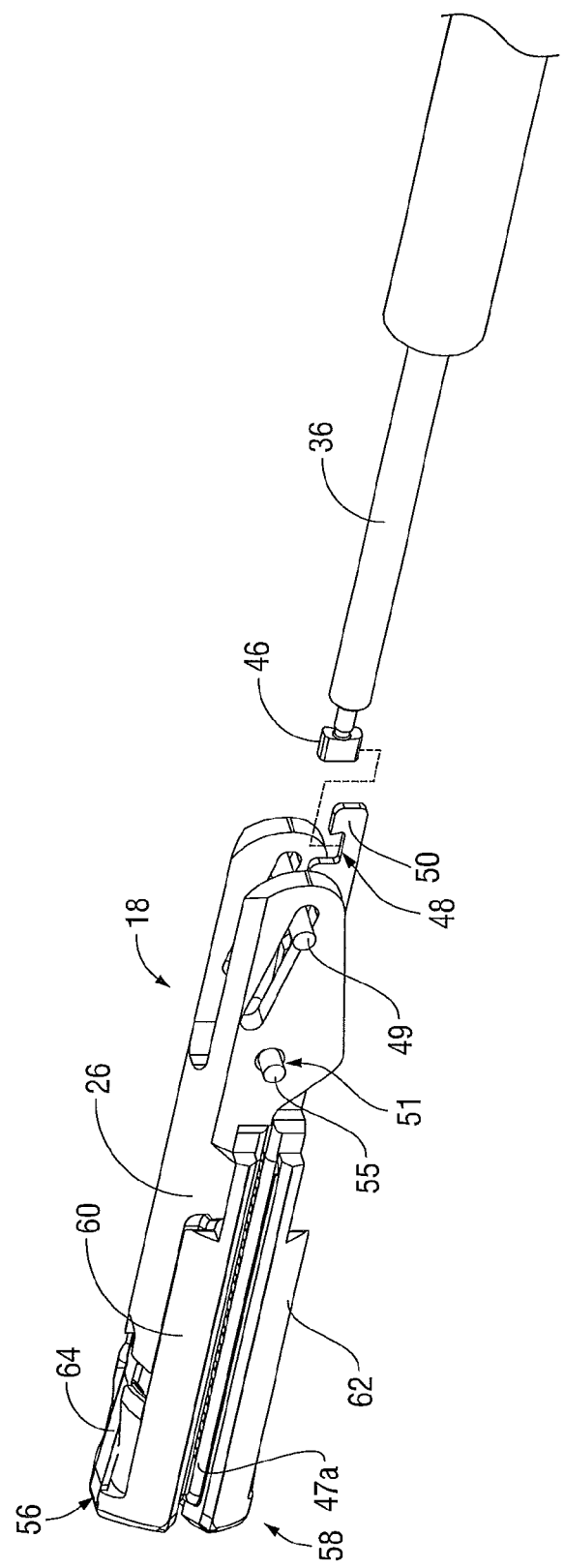
FIG. 15 is a partial, left perspective view of the distal end of the endoscopic bipolar forceps with the jaw shaft tip removed to illustrate the knife blade shaft and knife blade engaged with one another when the jaw members are in a closed configuration and the knife blade shaft and knife blade are in an extended configuration.

Knife blade 34 includes a distal end 52 which, unlike proximal end 50 that releasably couples to knife blade shaft 36, includes a cutting edge 54 that is configured to sever tissue (e.g., tissue that has been electrosurgically treated (as best seen in FIG. 14)). Cutting edge 54 may be beveled, serrated or otherwise configured to facilitate severing electrosurgically treated tissue.

Electrode assembly 8 includes a first electrode housing 56 and a second electrode housing 58 (FIGS. 3-5, 7-8 and 11-15). First and second electrode housings 56, 58 include respective first and second electrodes 47*b*, 47*a* (FIGS. 11 and 13-15) that are operably coupled via one or more suitable coupling methods to respective first and second insulative substrates 60, 62 (FIGS. 3-5, 7-8 and 11-15). In embodiments, first and second electrodes 47*a*, 47*b* are coupled to first and second insulative substrates 60, 62 via an overmolding process that is utilized to form first and second electrode housings 56, 58 (FIGS. 3-5, 7-8 and 11-15).

One or both of the first and second electrode housings 56, 58 may include a lock tab 64 (FIGS. 3-5, 7-8 and 11-15) that is configured to selectively engage a corresponding notch 66 (FIGS. 3-5) on a corresponding one of the jaw members 26, 28. In the illustrated embodiment, lock tabs 64 are positioned on insulative substrate 60 of jaw member 26 and insulative substrate 62 of jaw member 28. Lock tabs 64 are configured to facilitate coupling first and second electrode housings 56, 58 to the jaw members 26, 28. In the illustrated embodiment, lock tabs 64 are substantially resilient and in the form of a t-clip (see FIGS. 3-5 for example). Lock tabs 64 are biased radially inwardly and configured to flex radially outward as electrode assembly 8 is being coupled to jaws 26, 28, described in greater detail below.

Figure 4:
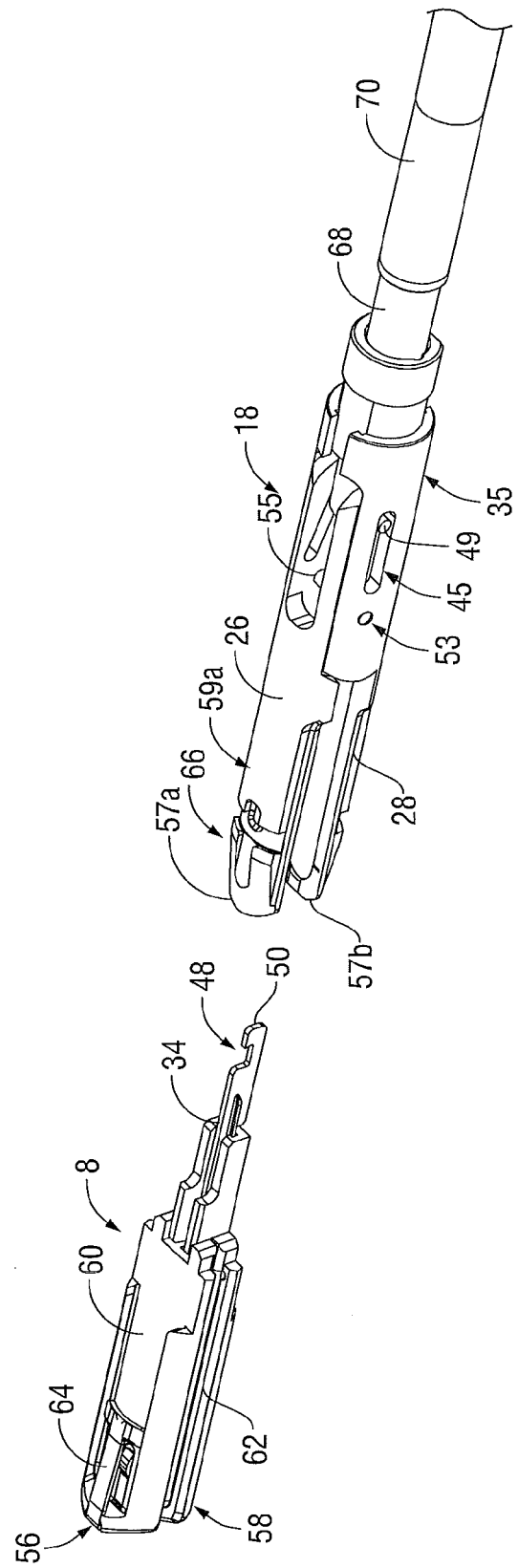
FIG. 4 is an enlarged perspective view of a distal end of the endoscopic bipolar forceps with an outer shaft removed.

Jaw members 26, 28 are supported at distal end 22 of shaft 20 via a jaw shaft tip 68 that is provided at a distal end of a jaw extension shaft 70 that is positioned within shaft 20 (FIG. 4). Jaw extension shaft 70 is configured to translate distally as a result of proximal movement of a movable handle 13 to move jaw 26 from a closed configuration (FIG. 1) to an open configuration (FIG. 11).

Jaws 26, 28 may be formed from any suitable type of material, e.g., metal, plastic, ceramic, etc. In the illustrative embodiment, jaws 26, 28 are formed from plastic and via an injection molding process.

Jaw members 26, 28 may be configured as a unilateral jaw configuration (as in the illustrated embodiment) wherein only one of the jaw members, e.g., jaw member 26, is movable for grasping tissue. Alternatively, jaw members 26, 28 may be configured as a bilateral jaw configuration wherein both of the jaws 26, 28 are movable to grasp tissue. In order to facilitate unilateral movement of jaw member 26 with respect to jaw member 28, jaw member 26 includes a bifurcated proximal end 25 (as best seen in FIG. 5) that includes two leg portions 27a, 27b each including a respective angled cam slot 29a, 29b. Moreover, jaw member 28 includes a proximal end 35 having a generally circumferential configuration that is configured to receive proximal end 25 of jaw member 26 therein (see FIG. 4 for example).

Left and right slots 45 are provided on left and right sides of proximal end 35 of jaw member 28 (see FIGS. 3-4); only left slot 45 is shown in the drawings. Slots 45 are configured to receive a cam pin 49 (FIGS. 3-4) therethrough. Moreover, left and right apertures 51 are provided on left and right sides of bifurcated proximal end 25 of jaw member 26 (FIGS. 5 and 7-8); only left aperture 51 is shown in the drawings. Further, left and right apertures 53 are provided on left and right sides of proximal end 35 of jaw member 28 (see FIGS. 3-4); only left aperture 53 is shown in the drawings. In assembled configuration, apertures 51, 53 are configured to receive a pivot pin 55 therethrough, see FIG. 4 for example.

Figure 7:
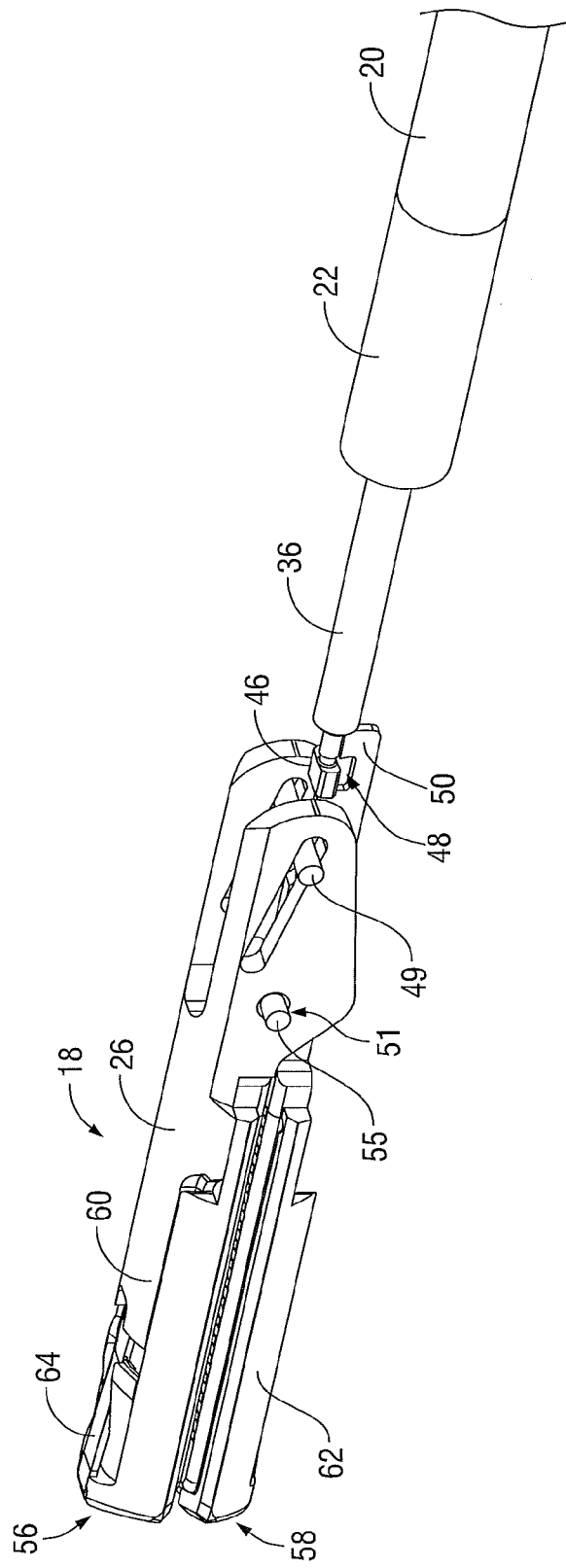
FIG. 7 is a partial, left perspective view of the distal end of the endoscopic bipolar with the jaw shaft tip removed to illustrate the knife blade shaft and the knife blade subsequent to loading of the electrode assembly and prior to engagement therebetween.
Figure 8:
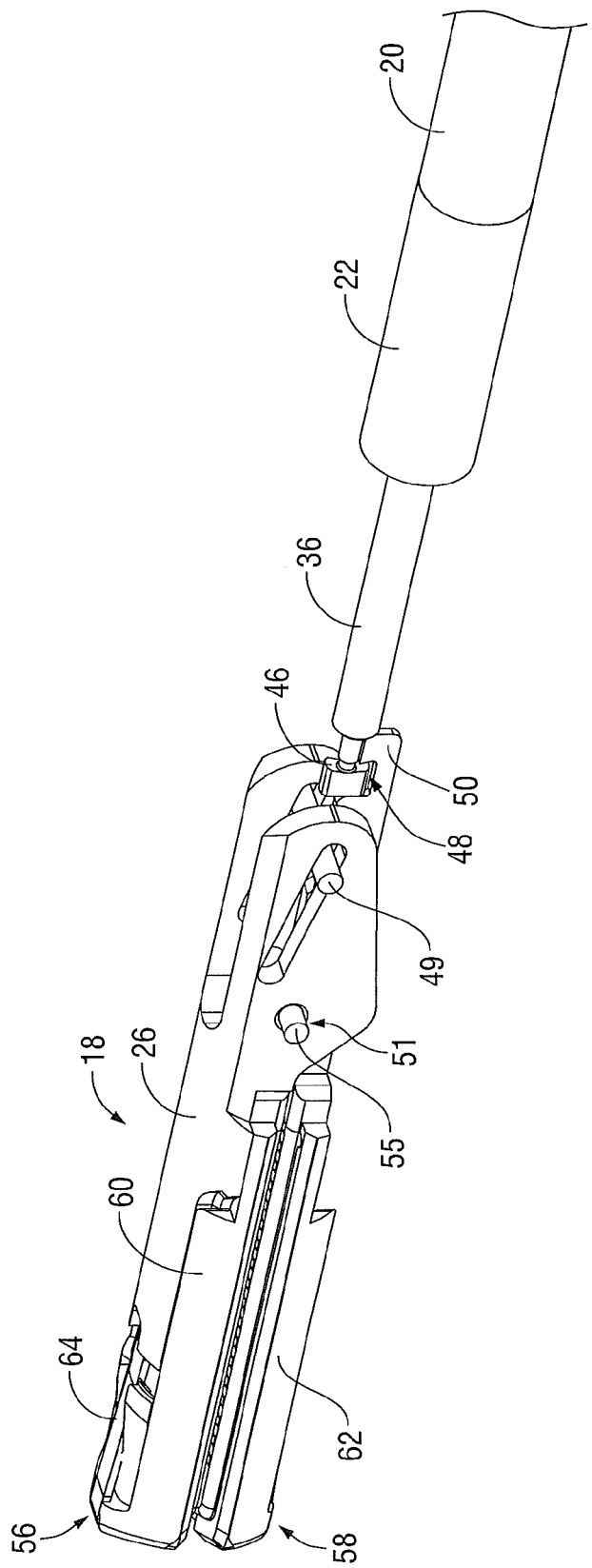
FIG. 8 is a partial, left perspective view of the distal end of the endoscopic bipolar with the jaw shaft tip removed to illustrate the knife blade shaft and knife blade engaged with one another.
Figure 9:
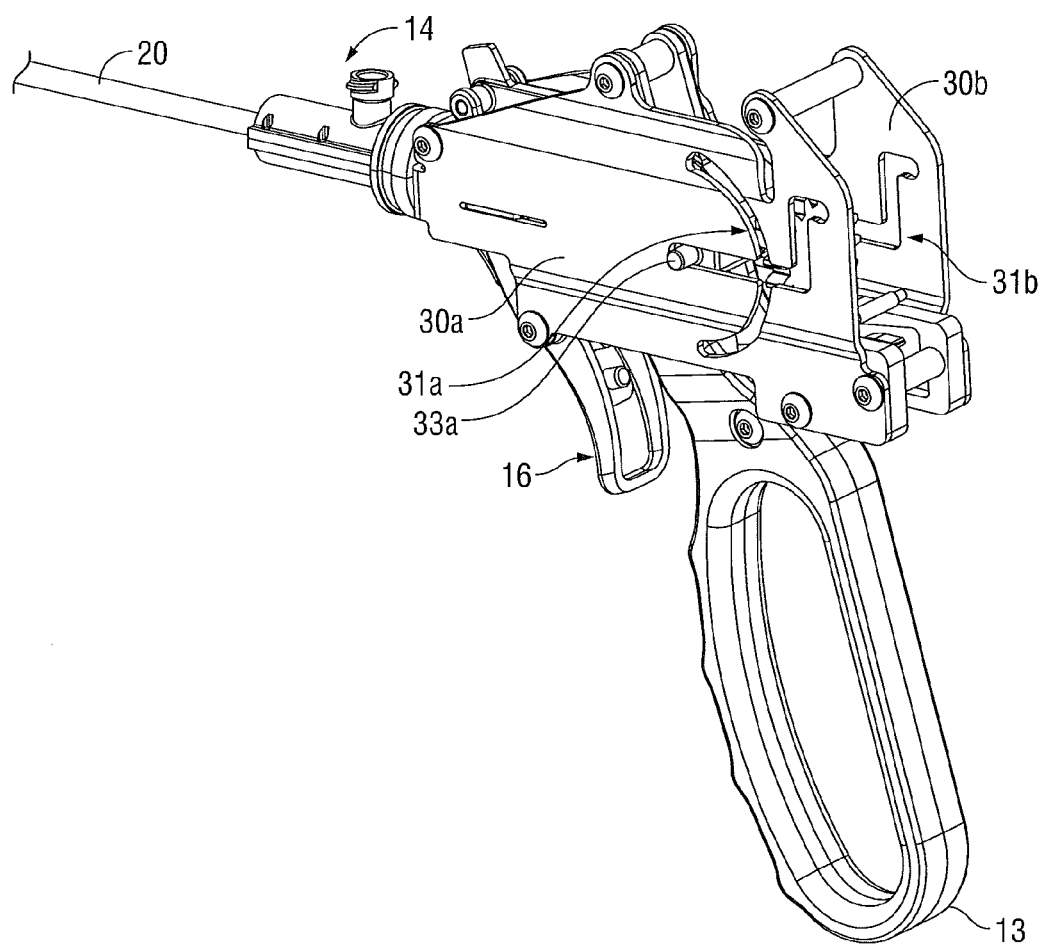
FIG. 9 is a partial, left perspective view of the proximal end of the endoscopic bipolar forceps illustrating a position of a trigger link when the electrode assembly is being loaded onto the endoscopic bipolar forceps.
Figure 10:
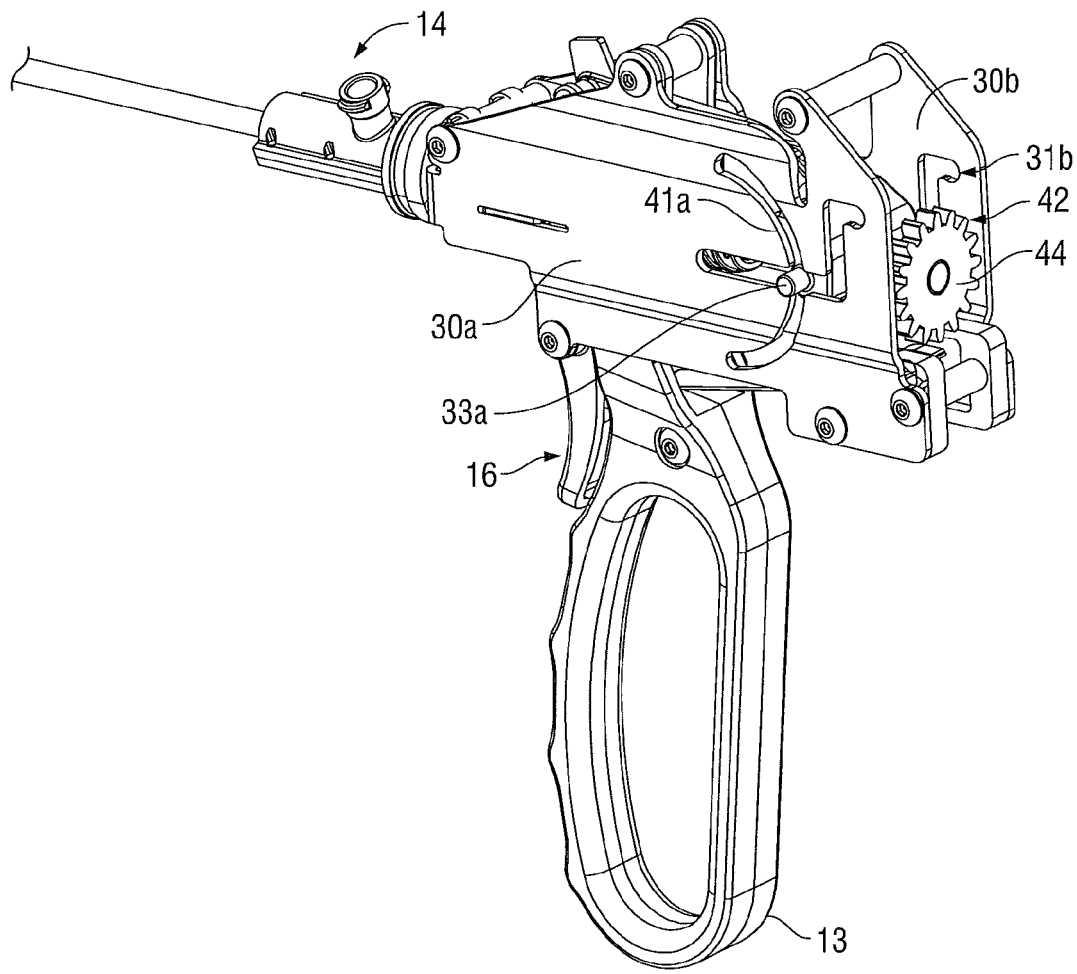
FIG. 10 is a partial, left perspective view of the proximal end of the endoscopic bipolar forceps.

Jaws 26, 28 each include a tapered distal end 57a, 57b (FIG. 4) that is configured to be received within a corresponding notched portion 59a (FIG. 4) provided on insulative substrate 60 and a corresponding notch portion (not explicitly shown) provided on insulative substrate 62. Notched portion 59a and the notched portion provided on insulative substrate 62 allow tapered distal ends 57a, 57b to slide therealong and engage lock tabs 64 to flex lock tabs 64 radially outwardly so that flex tabs 64 may engage corresponding notched portions 66 (FIGS. 7-8 and 10 illustrate lock tab 64 of first electrode housing 56 engaged with notch 66 of jaw member 26.

One or more electrical leads (not explicitly shown) are provided adjacent each of the jaw members 26, 28 and are configured to provide electrosurgical energy to first and second electrodes 47b, 47a. The electrical leads are provided adjacent jaw members 26, 28 in a manner that allows knife blade 34 to translate proximally and distally within jaw members 26, 28.

In use, electrode assembly 8 is packaged and shipped in a sterilized state. Similarly, forceps 6 and operative components associated therewith are also packaged and shipped in a sterilized state. To couple electrode assembly 8 including knife blade 34 to forceps 6, knife blade boss 46 may be placed in a pre-loaded configuration, see FIG. 7 for example. Knife blade 34 is positioned between jaw members 26, 28 and electrode assembly 8 is pushed proximally until lock tabs 64 engage notches 66.

Subsequently, selector switch 38 may be rotated to engage blade shaft spur gear 44, which, in turn, causes knife blade shaft 36 including knife blade boss 46 to rotate. A predetermined amount of rotation of knife blade boss 46 causes knife blade boss 46 to engage notch 48 of knife blade 34, see FIG. 11 for example.

With knife blade boss 46 and knife blade 34 engaged with one another, trigger 16 may be moved proximally to move knife blade 34 distally to sever electrosurgically treated tissue, see FIG. 14 for example. Thereafter, selector switch 38 may be moved to disengage knife blade boss 46 from knife blade 34 so that electrode assembly including knife blade 34 and/or forceps 6 may be sterilized for future use.

The unique configuration of a selectively removable electrode assembly 8 including knife blade 34 overcomes the aforementioned drawbacks that are typically associated with conventional forceps. Specifically, rather than disposing of forceps 6 after use, forceps 6 may be sterilized and re-used with a new electrode assembly 8 including a new knife blade 34 (or re-used with a previously used, but sterilized electrode assembly 8 including a new knife blade 34).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
 a housing having a shaft extending distally therefrom, the shaft defining a longitudinal axis therethrough;
 a knife blade shaft operably positioned within the shaft;
 an end effector operably disposed at a distal end of the shaft, the end effector including a pair of spaced-apart first and second jaw members movable from an open configuration to a clamping configuration; and
 an electrode assembly including first and second electrode housings and a knife blade, the first and second electrode housings operably coupled to one another and configured to selectively couple to respective first and second jaw members to electrosurgically treat tissue clamped between the first and second jaw members, the knife blade configured to selectively couple to the knife blade shaft such that rotation of the knife blade shaft relative to the shaft decouples the knife blade shaft from the knife blade, wherein a distal end of the knife blade shaft includes a mechanical interface configured to releasably couple to a corresponding mechanical interface disposed at a proximal end of the knife blade, the at least one mechanical interface on the knife blade in the form of a notch and the corresponding mechanical interface on the knife blade shaft in the form of a boss having a shape that complements the notch, the knife blade shaft rotatable about the longitudinal axis and relative to the knife blade to allow the boss to engage the notch of the knife blade.

2. An electrosurgical forceps according to claim 1, wherein the electrosurgical forceps includes a trigger assembly that operably couples to the knife blade shaft for moving the knife blade shaft and knife blade along the longitudinal axis.

3. An electrosurgical forceps according to claim 1, wherein the electrosurgical forceps includes a selector switch that is configured to rotate the knife blade shaft relative to the knife blade.

4. An electrosurgical forceps according to claim 3, wherein the selector switch includes a plurality of teeth that are configured to mesh with a blade shaft spur gear disposed at a proximal end of the knife blade shaft.

5. An electrosurgical forceps according to claim 1, wherein at least one of the first and second electrode housings includes a lock tab that is configured to selectively, removably engage a corresponding notch on at least one of the first and second jaw members to facilitate coupling and decoupling the first and second electrode housings to the first and second jaw members.

6. An electrosurgical forceps according to claim 5, wherein the lock tab is resilient and in the form of a t-clip.

7. An electrosurgical forceps according to claim 5, wherein the lock tab is positioned on an insulative substrate of the at least one first and second jaw member.

8. An electrosurgical forceps, comprising:
a housing having a shaft extending distally therefrom, the shaft defining a longitudinal axis therethrough;
a knife blade shaft operably positioned within the shaft and rotatable about the longitudinal axis; and
an end effector including a pair of spaced-apart first and second jaw members movable from an open configuration to a clamping configuration;
an electrode assembly including first and second electrode housings and a knife blade, the first and second electrode housings configured to selectively, removably couple to respective first and second jaw members of the electrosurgical forceps for electrosurgically treating tissue clamped between the first and second jaw members, the knife blade including a proximal end configured to selectively couple and decouple to a distal end of the knife blade shaft when the knife blade shaft is rotated about the longitudinal axis relative to the shaft; and
a selector switch configured to rotate the knife blade shaft relative to the knife blade, the selector switch including a plurality of teeth configured to mesh with a blade shaft spur gear disposed at a proximal end of the knife blade shaft.

9. An electrosurgical forceps according to claim 8, wherein the electrosurgical forceps includes a trigger assembly that operably couples to the knife blade shaft for moving the knife blade shaft and knife blade along the longitudinal axis.

10. An electrosurgical forceps according to claim 8, wherein the distal end of the knife blade shaft includes mechanical interface that is configured to releasably couple to a corresponding mechanical interface disposed at the proximal end of the knife blade, wherein the mechanical interface on the knife blade is in the form of a notch and the corresponding mechanical interface on the knife blade shaft is in the form of a boss having a shape that complements the notch, wherein the knife blade shaft is rotatable about the longitudinal axis relative to the knife blade to allow the boss to engage the notch of the knife blade.

11. An electrosurgical forceps according to claim 8, wherein at least one of the first and second electrode housings includes a lock tab that is configured to selectively engage a corresponding notch on at least one of the first and second jaw members to facilitate slidingly coupling the first and second electrodes to the first and second jaw members, wherein the lock tab is resilient and in the form of a t-clip, wherein the lock tab is positioned on an insulative substrate of the at least one first and second jaw member.

12. A method for electrosurgically treating tissue, comprising:
providing an electrosurgical forceps including a housing having a shaft defining a longitudinal axis therethrough, a knife blade shaft operably positioned within the shaft and rotatable about the longitudinal axis, and an end effector including a pair of spaced-apart first and second jaw members movable from an open configuration to a clamping configuration;
sliding an electrode assembly including first and second electrode housings and a knife blade between the first and second jaw members, respectively, thereby removably coupling the electrode assembly to the first and second jaw members;
coupling the knife blade to the knife blade shaft; and
energizing electrodes of the electrode assembly to electrosurgically treat tissue.

13. A method according to claim 12, including severing the electrosurgically treated tissue with the knife blade.

14. A method according to claim 12, including:
providing a distal end of the knife blade shaft with at least one mechanical interface that is configured to releasably couple to at least one corresponding mechanical interface disposed at a proximal end of the knife blade; and
rotating the knife blade shaft relative to the shaft thereby decoupling the at least one mechanical interface of the knife blade shaft from the at least one corresponding mechanical interface of the knife blade.

15. A method according to claim 12, including providing at least one of the first and second electrode housings with a lock tab that is configured to selectively engage a corresponding notch on at least one of the first and second jaw members to facilitate coupling and decoupling the first and second electrode housings to the first and second jaw members.

* * * * *